United States Patent [19]

Bunno et al.

[11] Patent Number: 4,867,913
[45] Date of Patent: Sep. 19, 1989

[54] 12α-SUBSTITUTED PREGNA-1,4-DIENE-3,20-DIONES

[75] Inventors: Masayasu Bunno, Chiba; Hidemi Harada, Kurashiki; Masao Tsuji, Kurashiki; Tsutomu Sugiura, Kurashiki; Yoshihiro Ichihara, Kurashiki, all of Japan

[73] Assignee: Kuraray Co., Ltd., Kurashiki, Japan

[21] Appl. No.: 898,331

[22] Filed: Aug. 20, 1986

Related U.S. Application Data

[63] Continuation of Ser. No. 806,429, Dec. 9, 1985, abandoned, which is a continuation of Ser. No. 701,987, Feb. 12, 1985, abandoned, which is a continuation of Ser. No. 469,739, Feb. 25, 1983, abandoned.

[51] Int. Cl.$^4$ .............................................. C07J 1/00
[52] U.S. Cl. .............................................. 260/397.45
[58] Field of Search .................................... 260/397.45

[56] References Cited

PUBLICATIONS

Chemical Abstracts, vol. 102 (1985); #4459d; Bunno et al.
Chemical Abstracts, vol. 102 (1985); #79206c; Kuraray Co. Ltd.

Primary Examiner—Douglas W. Robinson
Assistant Examiner—Joseph A. Lipovsky
Attorney, Agent, or Firm—Burns, Doane, Swecker & Mathis

[57] ABSTRACT

12α-Substituted pregna-1,4-diene-3,20-diones, which are novel compounds, are provided. These compounds are useful as intermediates for the synthesis of antiinflammatory corticoids represented by prednisone, prednisolone, etc.

12 Claims, No Drawings

12α-SUBSTITUTED PREGNA-1,4-DIENE-3,20-DIONES

This application is a continuation of application Ser. No. 806,429, filed Dec. 9, 1985 now abandoned; which is a continuation of Ser. No. 701,987, filed Feb. 15, 1985, now abandoned; which is a continuation of Ser. No. 469,739, filed Feb. 25, 1983, now abandoned.

BACKGROUND OF THE INVENTION

1. Field of the Invention

This invention relates to 12α-substituted pregna-1,4-diene-3,20-diones of the general formula (I)

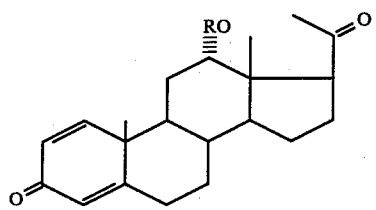

wherein R is a hydrogen atom, $R^1CO$ or $R^2SO_2$ where $R^1$ is a hydrogen atom, an alkyl group which may optionally be substituted or an aryl group which may optionally be substituted and $R^2$ is an alkyl group.

2. Description of the Prior Art

The 12α-substituted pregna-1,4-diene-3,20-diones of the general formula (I) as provided by the present invention are novel compounds not yet described in the literature but derived from 12α-hydroxypregna-1,4-dien-3-one-20-carbaldehyde, which is produced by allowing a specific microbe to act upon deoxycholic acid and/or a salt thereof, and can be used as intermediates for the synthesis of antiinflammatory corticoids represented by prednisone, prednisolone, etc.

The so-far known process for producing prednisone starts with deoxycholic acid and involves twenty-odd steps [L. F. Fieser and M. Fieser: Steroids, pages 634–647, Reinhold, 1959]. However, as the reagents required are expensive and the process is time-consuming, the process is not fully satisfactory for industrial application.

Some of the present inventors found a method of producing 12α-hydroxypregna-1,4-dien-3-one-20-carbaldehyde with high selectivity and in high yield which comprises cultivating, in a medium containing deoxycholic acid and/or a salt thereof, a microbe belonging to the genus Alcaligenes which is capable of producing 12α-hydroxypregna-1,4-dien-3-one-20-carbaldehyde by utilizing deoxycholic acid and/or a salt thereof as the substrate.

SUMMARY OF THE INVENTION

It is an object of the present invention to provide novel 12α-substituted pregna-1,4-diene-3,20-diones derived from 12α-hydroxypregna-1,4-dien-3-one-20-carbaldehdye which is obtained with the aid of a microbe.

It is another object of the present invention to provide novel 12α-substituted pregna-1,4-diene-3,20-diones which are useful as intermediates for the synthesis of various corticoids.

It is further object of the present invention to provide novel 12α-substituted pregna-1,4-diene-3,20-diones which are of use as advantageous intermediates for the synthesis of prednisone or prednisolone.

These objects as well as other objects and advantages of the present invention will become apparent to those skilled in the art from the following detailed description.

DETAILED DESCRIPTION OF THE INVENTION

Referring to the above general formula (I), R is a hydrogen atom, $R^1CO$ or $R^2SO_2$, wherein $R^1$ is a hydrogen atom, an alkyl group which may optionally be substituted such as methyl, chloromethyl, ethyl, 2-chloroethyl, propyl, hexyl, octyl, etc., or an aryl group which may optionally be substituted such as phenyl, o-, m- or p-tolyl, o-, m- or p-nitrophenyl, o-, m- or p-chlorophenyl, o-, m- or p-bromophenyl, α- or β-naphthyl, etc. and $R^2$ is an alkyl group such as methyl, ethyl, octyl, etc.

A 12α-substituted pregna-1,4-diene-3,20-dione of the general formula (I) can be derived from 12α-hydroxypregna-1,4-dien-3-one-20-carbaldehyde in the following stepwise process.

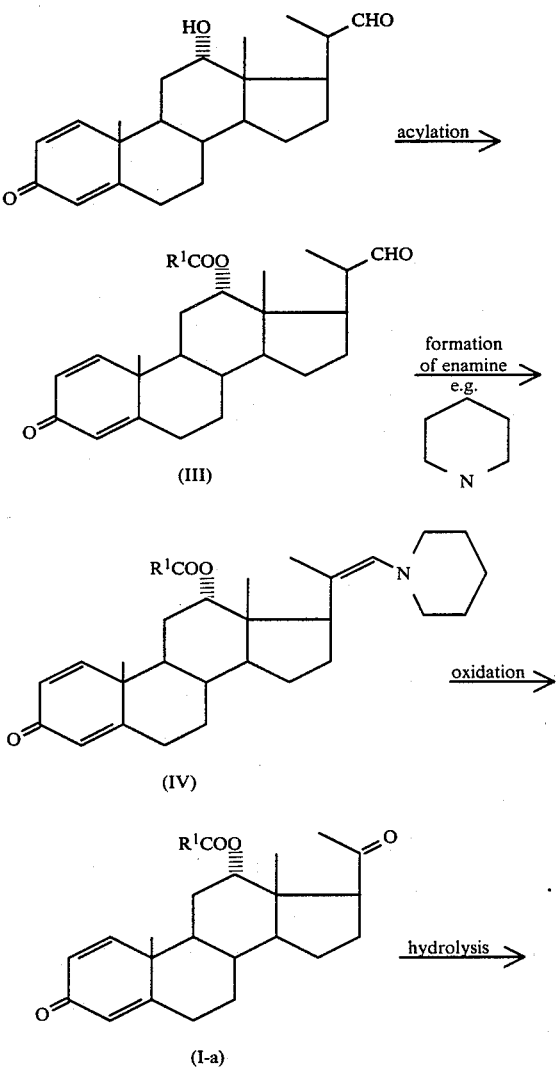

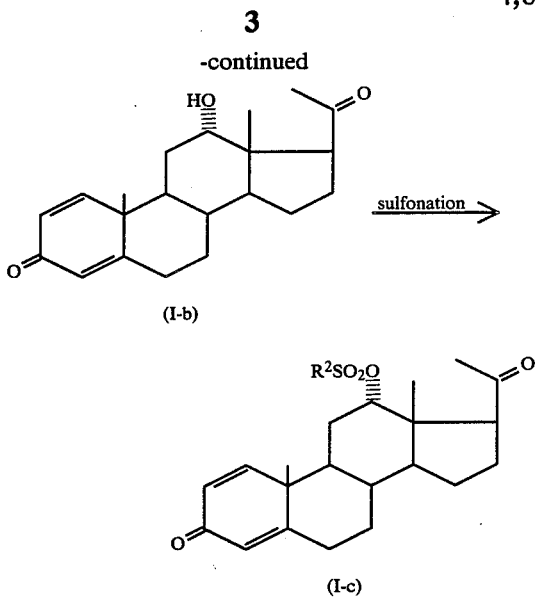

(I-b)

(I-c)

wherein $R^1$ and $R^2$ have the same meanings as defined in the general formula (I).

Thus, 12α-hydroxypregna-1,4-dien-3-one-20-carbaldehyde is reacted in the conventional manner with a carboxylic acid of the general formula (II)

$$R^1COOH \qquad (II)$$

wherein $R^1$ has the same meaning as defined in the general formula (I), or a reactive derivative thereof, e.g. acid halide, acid anhydride, etc. to give an 12α-acyloxypregna-1,4-dien-3-one-20-carbaldehyde of the general formula (III). The reaction of 12α-hydroxypregna-1,4-dien-3-one-20-carbaldehyde with chloride of carboxylic acid (II) which may be mentioned as a typical example is conducted in the presence of a tertiary amine such as triethylamine, pyridine, etc. This reaction is preferably carried out in a solvent, preferred examples of which are methylene chloride, chloroform or mixtures thereof with benzene, toluene, ethyl acetate, etc. While this reaction is generally conducted at room temperature, it may also be carried out under heating up to about 60° C., if necessary. After completion of the reaction, the reaction mixture is washed with diluted hydrochloric acid, aqueous sodium hydrogen carbonate or water, for instance, and after drying, low-boiling fractions are distilled off to give crude 12α-acyloxypregna-1,4-dien-3-one-20-carbaldehyde of the general formula (III). This crude compound can be directly submitted to the next reaction.

The 12α-acyloxypregna-1,4-dien-3-one-20-carbaldehyde (III) is then reacted with a secondary amine such as piperidine, pyrrolidine, morpholine, etc. to give an enamine of the general formula (IV). The secondary amine is used in a proportion of 1 to 2 molecular equivalents relative to 12α-acyloxypregna-1,4-dien-3-one-20-carbaldehyde (III). The water byproduced during the reaction is removed from the reaction system by refluxing with a solvent capable of forming an azeotrope with water, e.g. benzene or toluene. While this reaction does not always require a catalyst, it may be conducted in the presence of a catalyst such as p-toluenesulfonic acid. After completion of the reaction, the reaction mixture is distilled under reduced pressure to remove low-boiling fractions to give a crude enamine of the general formula (IV). This crude compound can be directly submitted to the next reaction.

The enamine (IV) may also be prepared by the steps of reacting 12α-hydroxypregna-1,4-dien-3-one-20-carbaldehyde with a secondary amine in the same manner as the above-mentioned reaction of an 12α-acyloxypregna-1,4-dien-3-one-20-carbaldehyde with a secondary amine and, then, reacting this enamine with a carboxylic acid of the general formula (II) or a reactive derivative thereof, which is preferably an acid anhydride, in the same manner as the reaction of 12α-hydroxypregna-1,4-dien-3-one-20-carbaldehyde with carboxylic acid (II) or a reactive derivative thereof.

The enamine of the general formula (IV) is oxidized with ozone or such an oxidizing reagent as chromium trioxide, pyridinium chlorochromate, sodium bichromate or the like to give an 12α-acyloxypregna-1,4-diene-3,20-dione of the general formula (I-a). The oxidation reaction using chromium trioxide is generally conducted in solvent pyridine. In this case, a mixture of chromium trioxide and pyridine is gradually added to a solution of enamine (IV) in pyridine or, alternatively, a solution of enamine (IV) in pyridine is gradually added to a mixture of chromium trioxide and pyridine. This oxidation reaction is conducted at temperaatures of about 0° C. to room temperature. After completion of the reaction, the reaction mixture is diluted with benzene, toluene or the like and filtered to remove solid matters. To the filtrate is added diluted hydrochloric acid, followed by extraction with benzene, toluene or the like. The extract is then distilled to remove low-boiling fractions to give a crude 12α-acyloxypregna-1,4-diene-3,20-dione of the general formula (I-a). This crude product is purified, if required, by silica gel column chromatography or recrystallization to give a high purity grade of 12α-acyloxypregna-1,4-diene-3,20-dione of the general formula (I-a).

This 12α-acyloxypregna-1,4-diene-3,20-dione (I-a) is then subjected to hydrolysis under conventional conditions to give 12α-hydroxypregna-1,4-diene-3,20-dione of the formula (I-b). For example, this hydrolysis reaction is carried out in a solvent such as methanol, ethanol or the like in the presence of potassium hydroxide or sodium hydroxide, for instance, at room temperature up to the reflux point of the solvent employed. After completion of the reaction, the reaction mixture is concentrated under reduced pressure, diluted with benzene or toluene, for instance, washed with water, diluted hydrochloric acid or the like, dried, and distilled to remove low-boiling fractions. The above procedure yields crude 12α-hydroxypregna-1,4-diene-3,20-dione of the formula (I-b). This crude product is recrystallized from ethyl acetate, for instance, to give a high purity grade of 12α-hydroxypregna-1,4-diene-3,20-dione.

The 12α-hydroxypregna-1,4-diene-3,20-dione is then sulfonated in the per se conventional manner to give the sulfonate of the general formula (I-c). For example, this sulfonation reaction is conducted by dissolving 12α-hydroxypregna-1,4-diene-3,20-dione in pyridine or picoline or a mixture thereof with benzene, toluene or the like, adding 1 to 2 molecular equivalents of a sulfonyl chloride of the general formula (V)

$$R^2SO_2Cl \qquad (V)$$

wherein $R^2$ has the same meaning as defined in the general formula (I), relative to 12α-hydroxypregna-1,4-diene-3,20-dione to the above resulting solution, and reacting them at room temperature or under warming up to about 80° C. After completion of the reaction, the reaction mixture is poured in diluted hydrochloric acid, for instance, and extracted with benzene or the like. The extract is washed with diluted hydrochloric acid, aqueous sodium hydrogen carbonate or water and, after drying, distilled to remove low-boiling fractions to give a crude sulfonate of the general formula (I-c). This crude product is for example recrystallized from ethyl acetate to give a high purity grade of sulfonate (I-c).

12α-Hydroxypregna-1,4-diene-3-one-20-carbaldehyde, which is a starting material for the production of 12α-substituted pregna-1,4-diene-3,20-diones of the general formula (I), is also a novel compound which has not been described in the literature, and can be produced by cultivating, in a medium containing deoxycholic acid and/or a salt thereof, a microbe belonging to the genus Alcaligenes and being capable of producing 12α-hydroxypregna-1,4-dien-3-one-20-carbaldehyde by utilizing deoxycholic acid and/or a salt thereof as the substrate.

As an example of said microbe of the genus Alcaligenes, there may be mentioned the strain *Alcaligenes faecalis* D4020-K15 (FERM BP-204). This strain is a mutant derived by mutagenic treatment from the parent strain *Alcaligenes faecalis* D4020 (FERM BP-182), which is a wild-type strain isolated from soil.

The morphological, cultural and physiological characteristics of the strains *Alcaligenes faecalis* D4020 and *Alcaligenes faecalis* D4020-K15 are summarized in Table 1.

TABLE 1

| Taxonomical character | *Alcaligenes faecalis* D4020 | *Alcaligenes faecalis* D4020-K15 |
|---|---|---|
| Morphological characteristics | | |
| Form | Rods | Rods |
| Size | $0.5 \times 1.2 \sim 1.7 \mu$ | $0.5 \times 1.0 \sim 1.7 \mu$ |
| Flagellum | Peritrichous flagella | Peritrichous flagella |
| Spore | Nil | Nil |
| Gram stain | Negative | Negative |
| Acid fast stain | Nil | Nil |
| Cultural characteristics | | |
| Bouillon agar plate culture | Circular, opaque, convex | Circular, opaque, convex |
| Bouillon agar slant culture | Moderate growth, filiform, pigment not produced | Moderate growth, filiform, pigment not produced |
| Bouillon broth | Moderate turbidity, pellicle | Moderate turbidity |
| Temperature for growth | Growth at 37° C., poor growth at 41° C. | Growth at 37° C., poor growth at 41° C. |
| Gelatin stab | No liquefaction | No liquefaction |
| Litmus milk | Alkaline, milk unchanged | Alkaline, milk unchanged |
| BCP milk | Alkaline, milk unchanged | Alkaline, milk unchanged |
| Physiological characteristics (Note 1) | | |
| Nitrate reduction | + | + |
| Denitrification | − | − |
| Methyl red test | − | − |
| Voges-Proskauer test | − | − |
| Indole production | − | − |
| Hydrogen sulfide production | − | − |
| Starch hydrolysis | − | − |
| Citrate utilization | + | + |
| Assimilation of inorganic nitrogen sources | + | + |
| Urease | ± | ± |
| Oxidase | + | + |
| Catalase | + | + |
| Require of oxygen | Aerobic | Aerobic |
| Oxidation/Fermentation test | Oxidative | Oxidative |

| Production of acids and gases from carbohydrates (Note 2) | Production of acids | Evolution of gases | Production of acids | Evolution of gases |
|---|---|---|---|---|
| (1) L-Arabinose | + | − | + | − |
| (2) D-Xylose | + | − | + | − |
| (3) D-Glucose | + | − | + | − |
| (4) D-Mannose | + | − | + | − |
| (5) D-Fructose | − | − | − | − |
| (6) D-Galactose | + | − | + | − |
| (7) Maltose | − | − | − | − |
| (8) Sucrose | − | − | − | − |
| (9) Lactose | − | − | − | − |
| (10) Trehalose | − | − | − | − |
| (11) D-Sorbitol | − | − | − | − |
| (12) D-Mannitol | − | − | − | − |
| (13) Inositol | − | − | − | − |
| (14) Glycerol | − | − | − | − |

| (15) Starch | — | — | — | — |

Remarks:
Note 1
The symbols used under Physiological characteristics indicate the following:
+: The strain has the corresponding characteristics or produces the corresponding product.
±: It is difficult to determine whether the strain has the corresponding characteristics or produces the corresponding product or not.
—: The strain neither has the corresponding characteristics nor produces the corresponding product.
Note 2
By using Hugh and Leifson medium in which each of the carbohydrates shown in Table 1 and Table 2 was used in lieu of the carbon source thereof, production of acids and gases by the strain was observed.
+: An acid or a gas is produced.
±: It is difficult to determine whether an acid or a gas is produced or not.
—: Neither an acid nor a gas is produced.

On the basis of these morphological, cultural and physiological characteristics, the strains have been classified according to Bergey's Manual of Determinative Bacteriology, 7th and 8th Editions.

The strain *Alcaligenes faecalis* D4020 has been identified as a strain of the genus Alcaligenes based on its morphological characteristics, among others, that it is a rod having peritrichous flagella and that it reacts negative in Gram staining as well as on the physiological characteristics, among others, that it reacts positive in the oxidase and catalase reactions, that it is aerobic and that the oxidation/fermentation test gives oxidative results, and further identified as a strain of the species *Alcaligenes faecalis* based on the facts that it does not liquefy gelatin, that milk becomes alkaline but otherwise remains unchanged and that it does not cause denitrification. Generally, a mutant is considered to belong to the same species as its parent strain belongs to. Accordingly, the strain *Alcaligenes faeclis* D4020-K15 has been judged as belonging to the species *Alcaligenes faecalis*.

In the above microbial process, deoxycholic acid per se can be used as the substrate. There can also be used an alkali metal salt of deoxycholic acid such as sodium deoxycholate, potassium deoxycholate or the like or an alkaline earth metal salt of deoxycholic acid such as calcium deoxycholate, magnesium deoxycholate or the like; preferred is an alkali metal salt. When a deoxycholate is used, it is dissolved in water to prepare an aqueous solution containing the deoxycholate in a predetermined concentration. Alternatively, a certain amount of an alkali metal compound or an alkaline earth metal compound which forms a salt with deoxycholic acid may previously be dissolved in water and thereto is added deoxycholic acid to give an aqueous solution containing a deoxycholate in a predetermined concentration.

In general, the concentration of the substrate in a culture medium may be varied widely in the range of from about 1 to 200 g/l as deoxycholic acid. However, from the viewpoints of the yield of the 12α-hydroxypregna-1,4-dien-3-one-20-carbaldehyde, cultivation conditions and economic efficiency such as operability or workability, it is preferable to use the substrate in a concentration of about 2 to 50 g/l as deoxycholic acid.

The cultivation can be carried out according to a known method under aerobic conditions and shake or submerged culture using a liquid medium is generally employed.

As the medium, there can be used one containing nutrients which can be assimilated by the microbe to be used. The medium may contain deoxycholic acid or a salt thereof as the sole carbon source. Optionally, it may contain an additional carbon source such as glucose, glycerol, peptone, meat extract, yeast extract, etc. or a mixture thereof. Generally, the additional carbon source can be added to the medium in a concentration of about 0.1 to 20 g/l. As a nitrogen source, there can be used an inorganic nitrogen source such as ammonium sulfate, ammonium chloride, ammonium phosphate, ammonium nitrate, sodium nitrate, potassium nitrate, etc.; an organic nitrogen source such as polypeptone, peptone, meat extract, etc.; or a mixture thereof. Generally, the nitrogen source can be added to the medium in a concentration of about 0.5 to 5 g/l. In addition, an inorganic salt such as dipotassium hydrogen phosphate, potassium dihydrogen phosphate, magnesium sulfate, manganese sulfate, zinc sulfate, cobalt chloride, sodium molybdate, cupric sulfate, calcium chloride, sodium chloride, etc. or a mixture thereof can be added to the medium.

The cultivation conditions are not very critical. Generally, the cultivation can be carried out in the manner of shake or submerged culture at a pH of about 7 to 9 at about 25° to 35° C. for about 10 hours to 7 days to cause production and accumulation of the 12α-hydroxypregna-1,4-dien-3-one-20-carbaldehye in the medium.

The 12α-hydroxypregna-1,4-dien-3-one-20-carbaldehyde thus accumulated in the culture broth is by far less soluble in water than the substrate deoxycholic acid or its salt and is generally precipitated out in the broth. To harvest this 12α-hydroxypregna-1,4-dien-3-one-20-carbaldehyde, the precipitated 12α-hydroxypregna-1,4-dien-3-one-20-carbaldehyde is separated from the broth containing suspended cells either by decanting or by the steps of centrifuging the broth at the speed that will not cause sedimentation of the suspended cells to additionally obtain a sediment of 12α-hydroxypregna-1,4-dien-3-one-20-carbaldehyde and then decanting. From the remaining broth, the cells and other insoluble matters are removed by filtration or centrifugation and the resulting filtrate or supernatant is made alkaline with an alkali such as sodium hydroxide, potassium hydroxide or calcium hydroxide, for instance, followed by extraction with a water-immiscible organic solvent capable of dissolving said aldehyde, e.g. ethyl acetate, chloroform or a mixture of chloroform and methanol. The extracts are pooled and the solvent is distilled off, whereby 12α-hydroxypregna-1,4-dien-3-one-20-carbaldehyde still remaining dissolved in the broth is recovered. The above extraction with an organic solvent can be applied not only to the filtrate or supernatant but also to the broth as such. The sediment or extract obtained in the above manner is substantially free from residues of the substrate deoxycholic acid and/or a salt thereof or any byproducts, so that a high purity grade of 12α-hydroxypregna-1,4-dien-3-one-20-carbaldehyde can be easily recovered therefrom, for example by recrystallization from aqueous methanol.

The sulfonate (I-c) provided by the present invention is subjected to elimination reaction of sulfonic acid to give pregna-1,4,11(12)-triene-3,20-dione which is a known compound. This elimination reaction is generally conducted in the presence of a reaction promoting agent, i.e. a compound which accepts sulfonic acid, such as potassium acetate, lithium chloride, collidine, potassium t-butoxide, etc. The proportion of the reaction promoting agent is about 1 to 20 molecular equivalents relative to the sulfonate (I-c). This reaction is preferably carried out in a solvent such as hexamethylphosphoramide, N,N-dimethylformamide, etc., generally under heating at about 80° to 140° C. Pregna-1,4,11(12)-triene-3,20-dione can also be prepared by subjecting an 12α-acyloxypregna-1,4-diene-3,20-dione (I-a) provided by the present invention to elimination reaction of carboxylic acid under heating. Pregna-1,4,11(12)-triene-3,20-dione can be converted to prednisone and, further, to prednisolone in the conventional manner, for example by the routes shown below by way of reaction formulas.

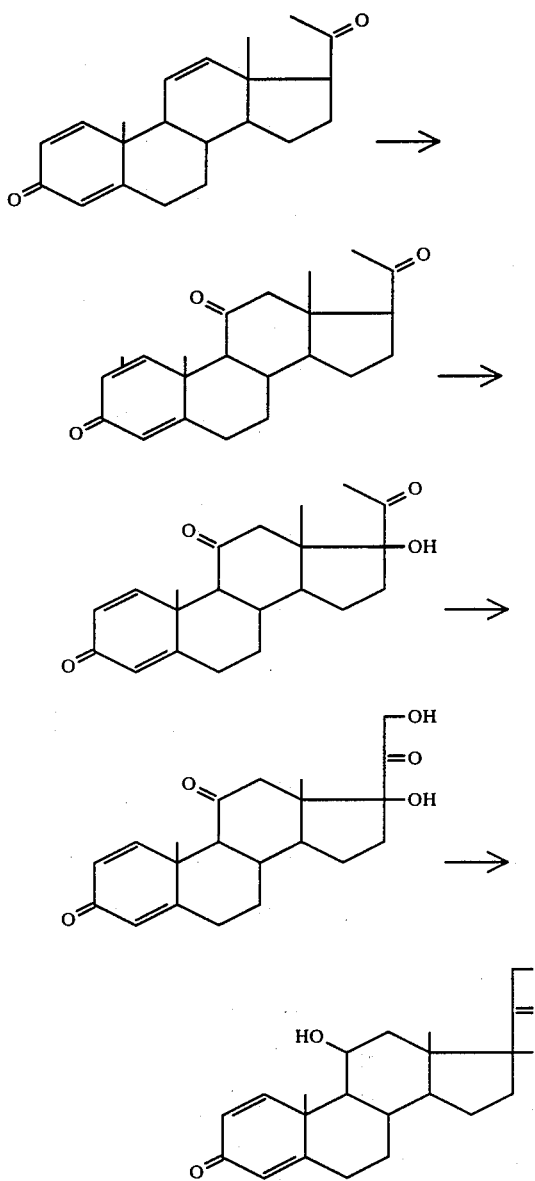

The following examples and reference examples further illustrate the present invention in detail but are not to be construed to limit the scope thereof.

PREPARATION OF MUTANTS

Preparation of the strain *Alcaligenes faecalis* D4020-K15

*Alcaligenes faecalis* D4020 was grown on a slant of medium 1 (composition: 0.5% deoxycholic acid, 0.05% sodium hydroxide, 0.5% peptone, 0.5% yeast extract, 0.5% sodium chloride and 1.5% agar). A loopful of the microbe so grown was used for inoculating 10 ml of medium 2 (composition: 2% deoxycholic acid, 0.2% sodium hydroxide, 0.2% ammonium nitrate, 0.1% potassium dihydrogen phosphate, 0.6% dipotassium hydrogen phosphate, 0.02% magnesium sulfate heptahydrate and 0.02% yeast extract) preliminarily prepared in a test tube (200 mm×21 mm in diameter), and shake-cultured at 30° C. for 8–10 hours. A 0.3-ml-portion of the culture was added to 10 ml of medium 3 (composition: 0.5% deoxycholic acid, 0.05% sodium hydroxide, 0.1% glucose, 0.2% ammonium nitrate, 0.1% potassium dihydrogen phosphate, 0.6% dipotassium hydrogen phosphate, 0.02% magnesium sulfate heptahydrate and 0.02% yeast extract) preliminarily prepared in a test tube (200 mm×21 mm in diameter), followed by incubation at 30° C. for 10–15 hours. The cells, which were in the logarithmic growth phase, were collected aseptically by filtration using a membrane filter (pore size: 0.45μ), washed with 20 ml of 0.1M phosphate buffer (pH 7.0) and suspended in 25 ml of the same buffer. To the suspension was added N-methyl-N'-nitro-N-nitrosoguanidine to a final concentration of 20 μg/ml. The mixture was shaken at 30° C. for 10–15 minutes. The cells so subjected to mutagenic treatment were collected by filtration using a membrane filter (pore size: 0.45μ), washed with 20 ml of 0.1M phosphate buffer (pH 7.0) and suspended in 20 ml of the same buffer. The resulting suspension was diluted with sterilized physiological saline solution and the dilution was applied to an agar plate made of medium 4 (composition: 0.5% deoxycholic acid, 0.05% sodium hydroxide, 0.2% ammoniun nitrate, 0.1% potassium dihydrogen phosphate, 0.6% dipotassium hydrogen phosphate, 0.02% magnesium sulfate heptahydrate, 0.02% yeast extract and 1.5% agar) so that 500 to 1,000 colonies could appear on the plate. The incubation was then performed at 30° C. for 3–4 days. Among the colonies that had appeared, pin point colonies were transferred to a slant made of medium 1, and one loopful thereof was used to inoculate 10 ml of medium 5 (composition: 0.2% deoxycholic acid, 0.02% sodium hydroxide, 0.1% glucose, 0.2% ammonium nitrate, 0.1% potassium dihydrogen phosphate, 0.6% dipotassium hydrogen phosphate, 0.02% magnesium sulfate heptahydrate and 0.02% yeast extract) preliminarily prepared in a test tube (200 mm×21 mm in diameter), followed by shake culture at 30° C. for 24 hours. The products in each culture obtained in this manner were examined by thin layer chromatography. A strain capable of selectively accumulating 12α-hydroxypregna-1,4-dien-3-one-20-carbaldehyde under the above cultural conditions was found and named *Alcaligenes faecalis* D4020-K15.

Reference Example 1

*Alcaligenes faecalis* D4020-K15 (FERM BP-204) was cultivated in the following manner. A medium (pH 8.4) was prepared by adding tap water to 1.0 g of deoxycholic acid, 0.1 g of glucose, 0.2 g of ammonium nitrate, 0.12 g of potassium dihydrogen phosphate, 0.61 g of dipotassium hydrogen phosphate, 0.02 g of magnesium sulfate heptahydrate, 0.02 g of yeast extract and 0.1 g of sodium hydroxide, to a volume of 100 ml. A 10 ml portion of this medium was placed in each of 10 test tubes (200 mm×21 mm in diameter) and steam-sterilized at 120° C. for 15 minutes. Separately and in advance, the above strain was grown in the same medium as above on a test tube shaker for one day, and a 0.5 ml portion of the thus obtained seed culture was added to each of the above-mentioned test tubes (200 mm×21 mm in diameter) and shake-cultured at 30° C. for 2 days. The pooled culture broth was centrifuged, whereby a mixture of the cells and a precipitate which had formed in the course of cultivation was separated from a culture supernatant. To said mixture was added a 1N aqueous solution of sodium hydroxide to adjust the resulting mixture to pH 9, and the mixture was extracted with 200 ml of ethyl acetate. Separately, the culture supernatant was adjusted to pH 9 by adding a 1N aqueous solution of sodium hydroxide, and extracted with 200 ml of ethyl acetate. This extract and the extract obtained in the above extraction were combined and dried over anhydrous sodium sulfate, and the ethyl acetate was distilled off using a rotary evaporator to give 750 mg of a mixture of 12$\beta$-hydroxypregna-1,4-dien-3-one-20-carbaldehyde and 12$\alpha$-hydroxypregna-1,4-dien-3-one-20-carbaldehyde.

A portion of the thus-obtained mixture was taken, and methanol was added thereto to prepare a 1% solution. A 25-$\mu$l portion of this solution was injected into a high performance liquid chromatograph equipped with a $\mu$Bondapek C-18 column (HLC-GPC-244 type manufactured by Waters Associates in U.S.A.). A 25:75 (by volume) water-methanol mixture adjusted to pH 4.0 was used as the mobile phase at a flow rate of 1 ml/minute. The detection was made by the refractive index method. The areas of the chromatographic peaks obtained were measured with an integrator (Shimadzu Chromato-Pack C-RIA manufactured by Shimadzu Corporation in Japan) and it was indicated that the peak areas for 12$\beta$-hydroxypregna-1,4-dien-3-one-20-carbaldehyde and 12$\alpha$-hydroxypregna-1,4-dien-3-one-20-carbaldehyde accounted for 95% of the total peak area. In the above mixture, the ratio between 12$\beta$-hydroxypregna-1,4-dien-3-one-20-carbaldehyde and 12$\alpha$-hydroxypregna-1,4-dien-3-one-20 carbaldehyde was ¼.

From the product mixture obtained according to the same procedure as mentioned above 12$\beta$-hydroxypregna-1,4-dien-3-one-20-carbaldehyde and 12$\alpha$-hydroxypregna-1,4-dien-3-one-20-carbaldehyde were respectively isolated in the following manner. First, a tubular column, 2.6 cm in inside diameter and 70 cm in length, was packed with a suspension of about 100 g of silica gel in about 200 ml of chloroform. Separately, 1.2 g of the above product mixture was dissolved in about 20 ml of chloroform and insolubles were removed. The chloroform solution was concentrated to about 5 ml and then allowed to be adsorbed on the above silica gel column and eluted in sequence with chloroform, a 99:1 (by volume) chloroform-ethanol mixture and a 97:3 (by volume) chloroform-methanol mixture. 12$\beta$-Hydroxypregna-1,4-dien-3-one-20-carbaldehyde was eluted in a fraction covering about the 250 ml to 280 ml portions of the second eluate, i.e. the 99:1 chloroform-ethanol mixture, and thereafter 12$\alpha$-hydroxypregna-1,4-dien-3-one-20-carbaldehyde was eluted with the same eluate in a fraction of about 450 ml to 510 ml. These two aldehydes were discriminated from each other based on the facts that, in thin layer chromatography using a thin layer plate (Silica gel 60, F-254 manufactured by Merck in U.S.A.) and an isooctaneethyl acetate-acetic acid mixture (10:10:2 by volume) as the developing solvent, 12$\beta$-hydroxypregna-1,4-dien-3-one-20-carbaldehyde gives a spot corresponding to $R_f$=about 0.4 and 12$\alpha$-hydroxypregna-1,4-dien-3-one-20-carbaldehyde gives a spot corresponding to $R_f$=about 0.34. The chloroform and ethanol were distilled off from each eluate fraction with a rotary evaporator, and the residue was washed with diethyl ether and dried. There were thus obtained about 80 mg of 12$\beta$-hydroxypregna-1,4-dien-3-one-20-carbaldehyde and about 360 mg of 12$\alpha$-hydroxypregna-1,4-dien-3-one-20-carbaldehyde.

The 12$\beta$-hydroxypregna-1,4-dien-3-one-20-carbaldehyde and 12$\alpha$-hydroxypregna-1,4-dien-3-one-20-carbaldehyde were identified based on the following data:

12$\beta$-Hydroxypregna-1,4-dien-3-one-20-carbaldehyde

Melting point: 157°–161° C.

Mass spectrum (m/Z): 342 [M]$\dot{+}$, 324 [M—H$_2$O]$\dot{+}$, 309 [M—H$_2$O—CH$_3$]$\dot{+}$ The presence of 3-keto-1,4-dien was confirmed by m/Z=121 and 122.

| NMR spectrum (90 MHz) $\delta_{HMS}^{DMSO-d6}$ |
| --- |
| 0.68 (3H, s) 18-CH$_3$ |
| 0.90 (3H, d, J = 6.3 Hz) 21-CH$_3$ |
| 1.16 (3H, s) 19-CH$_3$ |
| 3.25 (1H, s) 12$\beta$-OH |
| 3.40 (1H, m) 12$\alpha$-H |
| 5.95 (1H, s) 4-H |
| 6.15 (1H, dd, J = 18 Hz, J = 3 Hz) 2-H |
| 7.13 (1H, d, J = 12 Hz) 1-H |
| 9.50 (1H, d, J = 9 Hz) 22-CHO |

12$\alpha$-Hydroxpregna-1,4-dien-3-one-20-carbaldehyde

Melting point: 194°–201° C.,

Mass spectrum (m/Z): 342 [M]$\dot{+}$, 324 [M—H$_2$O]$\dot{+}$, 309 [M—H$_2$O—CH$_3$]$\dot{+}$ The presence of 3-keto-1,4-dien was confirmed by m/Z=121 and 122.

| NMR spectrum (90 MHz) $\delta_{HMS}^{DMSO-d6}$: |
| --- |
| 0.71 (3H, s) 18-CH$_3$ |
| 1.09 (3H, d) 21-CH$_3$ |
| 1.17 (3H, s) 19-CH$_3$ |
| 3.83 (1H, t, J = 3 Hz) 12$\beta$-H |
| 4.33 (1H, d) 12$\alpha$-OH |
| 5.95 (1H, s) 4-H |
| 6.08 (1H, d, J = 10 Hz) 2-H |
| 7.08 (1H, d, J = 10 Hz) 1-H |
| 9.56 (1H, s) 22-CHO |

EXAMPLE 1

Synthesis of 12$\alpha$-acetoxypregna-1,4-diene-3,20-dione

12$\alpha$-Hydroxypregna-1,4-dien-3-one-20-carbaldehyde (34.2 g) was dissolved in 300 ml of methylene chloride. To the solution were added 23.6 g of acetyl chloride and 27.7 g of pyridine, and the mixture was stirred at room temperature for 5 hours. To the reaction mixture was added 300 ml of methylene chloride, the resulting solution was washed in sequence with diluted hydrochloric acid and water, and dried over anhydrous magnesium sulfate. Low-boiling fractions were distilled off from the solution under reduced pressure. There was thus obtained crude 12α-acetoxypregna-1,4-dien-3-one-20-carbaldehyde as a viscous substance. This crude product was dissolved in 300 ml of benzene, 21.3 g of piperidine was added to the solution, and the resulting mixture was refluxed for 3 hours while removing the byproduct water azeotropically with benzene. Low-boiling fractions were distilled off from the thus-obtained reaction mixture. There remained crude 12α-acetoxy-22-(N-piperidyl)bisnor-1,4,20(22)-cholatrien-3-one as a viscous substance, which was dissolved in 180 ml of pyridine. To the solution was added gradually at room temperature a mixture of 20.0 g of chromium trioxide and 250 ml of pyridine. After stirring the resulting mixture for one hour, 1 liter of benzene was added to the reaction mixture. The solid matter was filtered off, and diluted hydrochloric acid was added to the filtrate. After effecting benzene extraction to a sufficient extent, the benzene layer was washed in sequence with diluted hydrochloric acid and water. Low-boiling fractions were distilled off under reduced pressure, and the residue was purified by preparation liquid chromatography [column: Waters Associates' Prep LC/System 500, Prep PAK ™ 500/SILICA; solvent system: isopropyl alcohol:n-hexane=20:80, v/v] to give 9.1 g of 12α-acetoxypregna-1,4-diene-3,20-dione as crystals. It has the following physical properties.

Melting point: 175°–176° C.

NMR spectrum (90 MHz) $\delta_{HMS}^{CDCl_3}$: 0.76, 1.20, 2.0, 2.06 (each s, each 3H); 5.10–5.22 (m, 1H); 6.07 (bs, 1H); 6.18, 6.20 (each d, 1H); 6.93 (d, 1H).

EXAMPLE 2

Synthesis of 12α-hydroxypregna-1,4-diene-3,20-dione

To a solution of 2.2 g of potassium hydroxide in 80 ml of methanol was added 7.4 g of 12α-acetoxypregna-1,4-diene-3,20-dione, and the mixture was stirred at room temperaature for 10 hours. The reaction mixture was concentrated to about one tenth the original volume by distilling off the methanol under reduced pressure. To the concentrated reaction mixture was added 150 ml of benzene, and the solution was washed in sequence with water, diluted hydrochloric acid and water and then dried over anhydrous magnesium sulfate. Low-boiling fractions were distilled off under reduced pressure and the residue was recrystallized from ethyl acetate to give 5.4 g of 12α-hydroxypregna-1,4-diene-3,20-dione (Gas chromatographic analysis revealed that purity thereof was 90%). It has the following physical properties.

Melting point: 185°–186° C.,

NMR spectrum (90 MHz) $\delta_{HMS}^{CDCl_3}$: 0.69, 1.17, 2.14 (each s, each 3H); 4.04–4.16 (m, 1H); 6.06 (bs, 1H); 6.16, 6.18 (each d, 1H); 7.03 (d, 1H).

EXAMPLE 3

Synthesis of 12α-mesyloxypregna-1,4-diene-3,20-dione

12α-Hydroxypregna-1,4-diene-3,20-dione (3.3 g) was dissolved in 17 ml of pyridine. To the solution was added 3.4 g of methanesulfonyl chloride, and the mixture was stirred at room temperature for 8 hours. The reaction mixture was then poured into 300 ml of diluted hydrochloric acid, and the resulting mixture was extracted with three 300 ml portions of benzene. The extracts were combined and washed in sequence with diluted hydrochloric acid, aqueous sodium bicarbonate solution and water, and dried over anhydrous magnesium sulfate. Low-boiling fractions were distilled off under reduced pressure from the extract to give 3.8 g of crude 12α-mesyloxypregna-1,4-diene-3,20-dione, which was recrystallized from ethyl acetate. The physical properties for the thus-purified product were as follows:

Melting point: 185°–186° C.,

NMR spectrum (90 MHz) $\delta_{HMS}^{CDCl_3}$: 0.82, 1.18, 2.10, 2.96 (each s, each 3H); 5.04–5.16 (m, 1H); 6.05 (bs, 1H); 6.19, 6.21 (each d, 1H); 6.95 (d, 1H).

EXAMPLES 4 TO 8

Synthesis of 12α-acyloxypregna-1,4-diene-3,20-dione (I-a)

The procedure followed in Example 1 was repeated except that propionyl chloride, n-butyryl chloride, benzoyl chloride, p-chlorobenzoyl chloride or chloroacetyl chloride was used in lieu of acetyl chloride to obtain 12α-propionyloxypregna-1,4-diene-3,20-dione, 12α-(n-butyryloxy)pregna-1,4-diene-3,20-dione, 12α-benzoyloxypregna-1,4-diene-3,20-dione, 12α-(p-chlorobenzoyloxy)pregna-1,4-diene-3,20-dione and 12α-chloroacetyloxypregna-1,4-diene-3,20-dione respectively. These products each have the following physical properties.

12α-propionyloxypregna-1,4-diene-3,20-dione

Melting point: 172°–173° C.,

NMR spectrum (90 MHz) $\delta_{HMS}^{CDCl_3}$: 0.75, 2.00 (each s, each 3H); 1.10, 1.20 (t, s, 6H); 5.10–5.22 (m, 1H); 6.07 (bs, 1H); 6.18, 6.20 (each d, 1H); 6.93 (d, 1H).

12α-(n-butyryloxy)pregna-1,4-diene-3,20-dione

Melting point: 143°–144° C.,

NMR spectrum (90 MHz) $\delta_{HMS}^{CDCl_3}$: 0.75, 1.18, 1.99 (each s, each 3H); 0.88 (t, 3H); 5.10–5.22 (m, 1H); 6.07 (bs, 1H); 6.17, 6.19 (each d, 1H); 6.92 (d, 1H).

12α-benzoyloxypregna-1,4-diene-3,20-dione

NMR spectrum (90 MHz) $\delta_{HMS}^{CDCl_3}$: 0.84, 1.21, 1.97 (each s, each 3H); 5.38–5.50 (m, 1H); 6.03–6.22 (m, 2H); 6.90 (d, 1H); 7.32–7.71 (m, 3H); 7.92–8.17 (m, 2H).

12α-(p-chlorobenzoyloxy)pregna-1,4-diene-3,20-dione

NMR spectrum (90 MHz) $\delta_{HMS}^{CDCl_3}$: 0.84, 1.20, 1.97 (each s, each 3H); 5.37–5.48 (m, 1H); 6.02–6.21 (m, 2H); 6.89 (d, 1H); 7.41 (d, 2H); 7.92 (d, 2H).

12α-chloroacetoxypregna-1,4-diene-3,20-dione

FD Mass spectrum (m/Z): 405 $[M+1]^+$, 311 $[M+1—ClCH_2CO_2H]^+$.

EXAMPLE 9

Synthesis of 12α-(n-butylsulfonyloxy)pregna-1,4-diene-3,20-dione

The procedure followed in Example 3 was repeated except that n-butylsulfonyl chloride was used in lieu of methanesulfonyl chloride to obtain 12α-(n-butylsulfonyloxy)pregna-1,4-diene-3,20-dione. This product was identified based on the following FD Mass analysis.

FD Mass spectrum (m/Z): 449 $[M+1]^+$, 311 $[M+1—Bu^nSO_3H]^+$.

REFERENCE EXAMPLE 2

Synthesis of pregna-1,4,11(12)-triene-3,20-dione

12α-Mesyloxypregna-1,4-diene-3,20-dione (3.0 g) was dissolved in 60 ml of hexamethylphosphoramide. To the solution was added 7.2 g of potassium acetate, and the mixture was stirred at 120° C. for 5 hours. To the reaction mixture was added 300 ml of diluted hydrochloric acid, and the whole mixture was extracted with three 200 ml portions of benzene. The extracts were combinedly washed in sequence with diluted hydrochloric acid and water, and dried over anhydrous magnesium sulfate. Low-boiling fractions were distilled off under reduced pressure and the residue was purified by silica gel column chromatography (eluent: acetone-n-hexane, 4:6 by volume) to give 1.6 g of pregna-1,4,11(12)-triene-3,20-dione as crystals. The physical properties for the obtained crystal were as follows:

Melting point: 167°–169° C.

NMR spectrum (90 MHz) $\delta_{HMS}^{CDCl_3}$: 0.74, 1.17, 2.15 (each s, each 3H); 5.66 (d, 1H); 6.07–6.40 (m, 3H); 7.12 (d, 1H).

What is claimed is:

1. A 12α-substituted pregna-1,4-diene-3,20-dione of the general formula

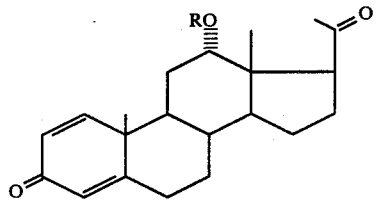

wherein R is a hydrogen atom, R¹CO or R²SO₂ where R¹ is a hydrogen atom, an alkyl group which may optionally be substituted or an aryl group which may optionally be substituted and R² is an alkyl group.

2. The 12α-substituted pregna-1,4-diene-3,20-dione as claimed in claim 1 which is an 12α-acyloxypregna-1,4-diene-3,20-dione of the general formula

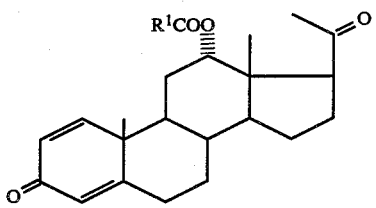

wherein R¹ is a hydrogen atom, an alkyl group which may optionally be substituted or an aryl group which may optionally be substituted.

3. The 12α-substituted pregna-1,4-diene-3,20-dione as claimed in claim 2 which is 12α-acetoxypregna-1,4-diene-3,20-dione.

4. The 12α-substituted pregna-1,4-diene-3,20-dione as claimed in claim 2 which is 12α-benzoyloxypregna-1,4-diene-3,20-dione.

5. The 12α-substituted pregna-1,4-diene-3,20-dione as claimed in claim 2 which is 12α-propionyloxypregna-1,4-diene-3,20-dione.

6. The 12α-substituted pregna-1,4-diene-3,20-dione as claimed in claim 2 which is 12α-(n-butyryloxy)pregna-1,4-diene-3,20-dione.

7. The 12α-substituted pregna-1,4-diene-3,20-dione as claimed in claim 2 which is 12α-(p-chlorobenzoyloxy)-pregna-1,4-diene-3,20-dione.

8. The 12α-substituted pregna-1,4-diene-3,20-dione as claimed in claim 2 which is 12α-chloroacetoxypregna-1,4-diene-3,20-dione.

9. The 12α-substituted pregna-1,4-diene-3,20-dione as claimed in claim 1 which is 12α-hydroxypregna-1,4-diene-3,20-dione.

10. The 12α-substituted pregna-1,4-diene-3,20-dione as claimed in claim 1 which is a sulfonate of the general formula

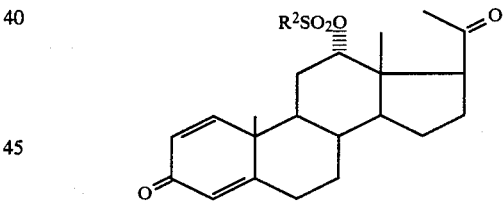

wherein R² is an alkyl group.

11. The 12α-substituted pregna-1,4-diene-3,20-dione as claimed in claim 10 which is 12α-mesyloxypregna-1,4-diene-3,20-dione.

12. The 12α-substituted pregna-1,4-diene-3,20-dione as claimed in claim 10 which is 12α-(n-butylsulfonyloxy)pregna-1,4-diene-3,20-dione.

* * * * *